(12) United States Patent
Moehring et al.

(10) Patent No.: US 7,128,713 B2
(45) Date of Patent: Oct. 31, 2006

(54) DOPPLER ULTRASOUND METHOD AND APPARATUS FOR MONITORING BLOOD FLOW AND HEMODYNAMICS

(75) Inventors: Mark A. Moehring, Seattle, WA (US); Joseph H. Farnsworth, Vassalboro, ME (US); Ajay Philip Zachariah, Bellevue, WA (US); Henry James Baron, Jr., Kirkland, WA (US)

(73) Assignee: Spentech, Inc., Seattle, WA (US)

( * ) Notice: Subject to any disclaimer, the term of this patent is extended or adjusted under 35 U.S.C. 154(b) by 268 days.

(21) Appl. No.: 10/618,090

(22) Filed: Jul. 10, 2003

(65) Prior Publication Data

US 2005/0033174 A1    Feb. 10, 2005

(51) Int. Cl.
*A61B 8/06* (2006.01)

(52) U.S. Cl. ..................................... 600/453
(58) Field of Classification Search ................ 600/437, 600/440, 441, 442, 443, 447, 450, 453, 454, 600/587; 73/615, 626; 128/916; 367/7, 367/11, 130, 138
See application file for complete search history.

(56) References Cited

U.S. PATENT DOCUMENTS

| | | | |
|---|---|---|---|
| 4,014,206 A | 3/1977 | Taylor | 73/19 |
| 4,152,928 A | 5/1979 | Roberts | 73/61 R |
| 4,319,580 A | 3/1982 | Colley et al. | 128/661 |
| 4,501,277 A | 2/1985 | Hongo | 128/660 |
| 4,751,929 A | 6/1988 | Hayakawa et al. | 128/663 |
| 4,800,891 A | 1/1989 | Kim | 128/661.09 |
| 4,848,354 A | 7/1989 | Angelsen et al. | 128/660.05 |
| 4,896,674 A | 1/1990 | Seo | 128/661.09 |
| 4,993,417 A | 2/1991 | Seo | 128/661.09 |
| 5,053,008 A | 10/1991 | Bajaj | 604/104 |
| 5,083,567 A | 1/1992 | Uchibori | 128/661.09 |
| 5,101,828 A * | 4/1992 | Welkowitz et al. | 600/481 |
| 5,103,826 A | 4/1992 | Bonnefous | 128/661.08 |
| 5,103,827 A | 4/1992 | Smith | 128/661.08 |
| 5,129,399 A | 7/1992 | Hirama | 128/661.01 |
| 5,148,808 A | 9/1992 | Satake | 128/660.05 |
| 5,231,573 A | 7/1993 | Takamizawa | 364/413.25 |
| 5,271,404 A | 12/1993 | Corl et al. | 128/661.08 |

(Continued)

FOREIGN PATENT DOCUMENTS

EP        0 079 453 A1    5/1983

(Continued)

OTHER PUBLICATIONS

Alexandrov, A.V. et al., "Insonation Method and Diagnostic Flow Signatures for Transcranial Power Motion (M-Mode) Doppler", Journal of Neuroimaging, vol. 12, No. 3, Jul. 2002. pp. 236-244.

(Continued)

*Primary Examiner*—Ali Imam
(74) *Attorney, Agent, or Firm*—Dorsey & Whitney LLP

(57) ABSTRACT

A pulse Doppler ultrasound system and associated methods are described for monitoring blood flow and hemodynamics. The Doppler ultrasound system includes an ultrasound probe to emit ultrasound signals and detect reflected signals therefrom and further includes a processor coupled to the ultrasound probe and operable to process the detected reflected signals and calculate therefrom blood flow data for a plurality of locations at time intervals, the processor further operable to identify locations at which blood flow having a hemodynamic characteristic is present based on the blood flow data calculated for a plurality of the time intervals. A user interface coupled to the processor provides blood flow information based on the blood flow data, the blood flow information representative of detected blood flow and the presence of the hemodynamic characteristic.

28 Claims, 10 Drawing Sheets
(1 of 10 Drawing Sheet(s) Filed in Color)

U.S. PATENT DOCUMENTS

| | | | | |
|---|---|---|---|---|
| 5,348,015 | A | 9/1994 | Moehring et al. | 128/661.07 |
| 5,441,051 | A | 8/1995 | Hileman et al. | 128/661.08 |
| 5,476,097 | A | 12/1995 | Robinson | 128/660.05 |
| 5,501,223 | A | 3/1996 | Washburn et al. | 128/661.09 |
| 5,513,640 | A | 5/1996 | Yamazaki et al. | 128/661.09 |
| RE35,371 | E | 11/1996 | Seo | 128/661.09 |
| 5,615,680 | A | 4/1997 | Sano | 128/661.09 |
| 5,622,173 | A | 4/1997 | Bisson et al. | 128/661.01 |
| 5,732,705 | A | 3/1998 | Yokoyama et al. | 128/660.07 |
| 5,785,654 | A | 7/1998 | Iinuma et al. | 600/441 |
| 5,785,655 | A | 7/1998 | Goodsell, Jr. et al. | 600/441 |
| 5,860,927 | A | 1/1999 | Sakaguchi et al. | 600/453 |
| 5,882,315 | A | 3/1999 | Ji et al. | 600/553 |
| 5,910,118 | A | 6/1999 | Kanda et al. | 600/455 |
| 5,913,824 | A | 6/1999 | Ogasawara et al. | 600/455 |
| 5,919,139 | A | 7/1999 | Lin | 600/443 |
| 5,997,478 | A | 12/1999 | Jackson et al. | 600/437 |
| 6,045,505 | A | 4/2000 | Holley et al. | 600/441 |
| 6,196,972 | B1 | 3/2001 | Moehring | 600/454 |
| 6,482,161 | B1 * | 11/2002 | Sumanaweera et al. | 600/454 |
| 6,503,202 | B1 | 1/2003 | Hossack et al. | 600/454 |
| 6,524,249 | B1 | 2/2003 | Moehring et al. | 600/438 |
| 6,547,736 | B1 | 4/2003 | Moehring et al. | 600/454 |
| 6,616,611 | B1 | 9/2003 | Moehring | 600/454 |
| 6,635,017 | B1 | 10/2003 | Moehring et al. | 600/439 |
| 2004/0138563 | A1 | 7/2004 | Moehring et al. | 600/439 |
| 2005/0075568 | A1 | 4/2005 | Moehring | 600/453 |

FOREIGN PATENT DOCUMENTS

| | | |
|---|---|---|
| WO | WO 94/06353 | 3/1994 |

OTHER PUBLICATIONS

Kisslo J.A., et al., "Color Flow Imaging", Echo inContext, Duke Center for Echo, www. echoincontext.com/doppler04/doppler04_01.asp, Duke University Medical Center, 2000. 30 pages.

Moehring, M.A. et al., "Power M-Mode Doppler (PMD) for Observing Cerebral Blood Flow and Tracking Emboli", Ultrasound in Medicine and Biology, vol. 28, No. 1, 2002. pp. 49-57.

*Aloka-860 Operational Manual.* vol. I System Description, Effective S/N: 51M8876 and above. pp. i-15-2 and A-2-A-5.

*Aloka Color Doppler Model SSD-860 Cardiovascular Scanner Sales Brochure.* Aloka Co., Ltd., Japan.

Demchuk, A.M. et al., "Thrombolysis in Brain Ischemia (TIBI) Transcranial Doppler Flow Grades Predict Clinical Serverity, Early Recovery, and Mortality in Patients Treated with Intravenous Tissue Plasminogen Activator", American Heart Association, Inc., Jan. 2001. pp. 89-93.

Duncan, Walter J. *Color Doppler in Clinical Cardiology.* Philadelphia, W.B. Saunders Company, Harcourt Brace Jovanovich, Inc., 1988. pp. 1-13.

Ferrera, K. et al., "Color Flow Mapping," Ultrasound in Medicine and Biology, vol. 23, No. 3, 1997, pp. 321-345.

Giller, C.A. et al., "Oscillations in Cerebral Blood Flow Detected with a Transcranial Doppler Index", Journal of Cerebral Blood Flow and Metabolism, vol. 19, No. 4, Apr. 1999. pp. 452-459.

Griffith, James M. et al., "An Ultrasound System for Combined Cardiac Imaging and Doppler Blood Flow Measurement in Man", Biomedical Engineering and Instrumentation Branch, Division of Research Services and the Cardiology Branch, National Heart, Lung, and Blood Institute, Maryland, vol. 57, No. 5, May 1978, pp. 925-930.

Iwase, Masatsugu et al. *Clinical Echocardiography.* Dordrecht, Kluwer Academic Publishers, 1989. pp. 11-27 and 250-281.

Kremkau, G.W. *Doppler Ultrasound, Principles and Instruments.* (Philadelphia, W.B. Saunders Company, 1990), pp. 177-211.

Missri, José*Clinical Doppler Echocardiography Spectral and Color Flow Imaging.* New York, McGraw-Hill, Inc., 1990. pp. 9-27 and 279-303.

Omoto, R. et al., "The Development of Real-Time Two-Dimensional Doppler Echocardiography and Its Clinical Significance in Acquired Valvular Diseases With Special Reference to the Evaluation of Valvular Regurgitation", Reprinted from *Japanese Heart Journal*, vol. 25, No. 3, pp. 325-340, May 1984.

Omoto, R. et al., "Clinical Significance and Prospects of Real-Time Two-Dimensional Doppler Echocardiography", Color ATLAS of Real-Time Two-Dimensional Doppler Echocardiography, Chapter 1-6, pp. 1-44, Shindan-To-Chiryo Co., Ltd. Tokyo 1984.

"Operation Manual for Diagnostic Ultrasound Equipment Model SSH-160A (2B730-405E*B)", Toshiba Corporation, 1987, pp. 7-4-7-5, 8-1, 11-1-11-3, 11-12, 12-1, 12-3 and 16-10.

Redel, Dierk A. *Color Blood Flow Imaging of the Heart.* Germany, Springer-Verlag Berlin Heidelberg, 1988. pp. 5-12 and 27-41.

Weyman, Arthur E. *Principles and Practice of Echocardiography*, 2d ed. Philadelphia, Lea & Febiger, 1994. pp. 218-233 and 256-281.

* cited by examiner

| PRF, kHz | D0, mm 502 | D1, mm 504 | D2, mm 506 | D3, mm 508 | MAX VELOC ON SPECTROGRAM DISPLAY cm/s |
|---|---|---|---|---|---|
| 8 | 11 | 96 | 107 | 192 | 308 |
| 12.5 | 11 | 61 | 72 | 122 | 480 |
| 15.625 | 11 | 49 | 60 | 98 | 600 |

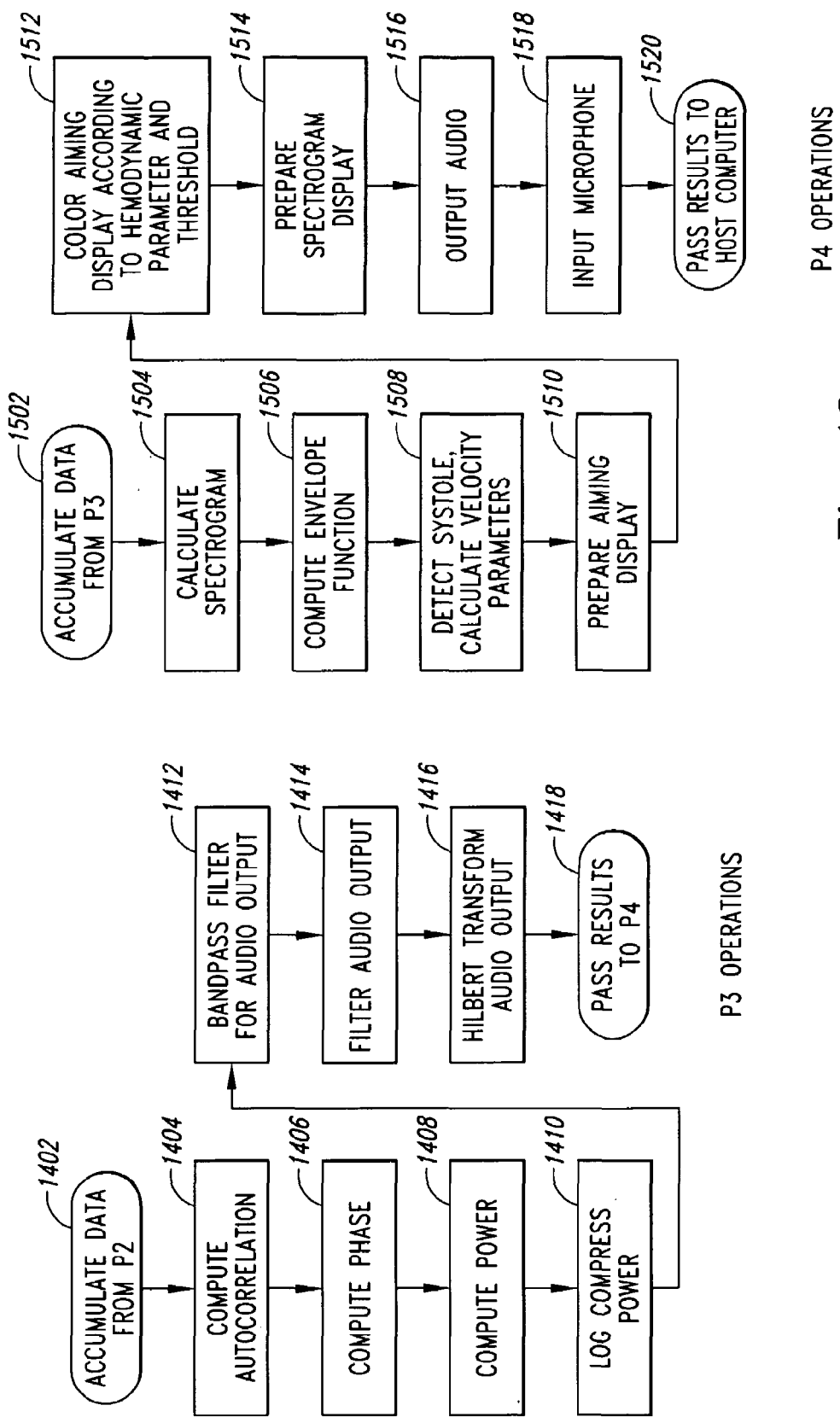

DOPPLER ULTRASOUND METHOD AND APPARATUS FOR MONITORING BLOOD FLOW AND HEMODYNAMICS

STATEMENT AS TO GOVERNMENT RIGHTS

The disclosed invention was made with support from the United States Government, which has certain fights in the invention pursuant to Grant No. 5R 44HL057108-03 awarded by the National Institutes of Health.

TECHNICAL FIELD

The invention relates generally to medical monitoring and diagnostic procedures and devices, and more particularly to a Doppler ultrasound method and apparatus for monitoring blood flow and hemodynamics.

BACKGROUND OF THE INVENTION

Doppler ultrasound has been used to measure blood flow velocity for many years. The well-known Doppler shift phenomenon provides that ultrasonic signals reflected from moving targets will have a shift in frequency directly proportional to the target velocity component parallel to the direction of the ultrasound beam. The frequency shift is the same for any object moving at a given velocity, whereas the amplitude of the detected signal is a function of the acoustic reflectivity of the moving object reflecting the ultrasound. Pulse Doppler ultrasound systems commonly produce a spectrogram of the detected return signal frequency (i.e., velocity) as a function of time in a particular sample volume, with the spectrogram being used by a physician to determine blood flow characteristics of a patient.

Typically, a user of ultrasound equipment finds it rather difficult to properly orient and position an ultrasound transducer or probe on the patient, as well as to select a depth along the ultrasound beam corresponding to the desired location where blood flow is to be monitored. This is particularly true in ultrasound applications such as transcranial Doppler imaging (TCD). The blood vessels most commonly observed with TCD are the middle, anterior, and posterior cerebral arteries, and the vertebral and basilar arteries. The Doppler transducer must be positioned so the ultrasound beam passes through the skull via the temporal windows for the cerebral arteries, and via the foramen magnum for the vertebral and basilar arteries. The user of the ultrasound equipment may find it difficult to locate these particular windows or to properly orient the ultrasound probe once the particular window is found.

A complicating factor in locating the ultrasound window is determination of the proper depth at which the desired blood flow is located. Commonly, the user does not know if he is looking in the correct direction at the wrong depth, the wrong direction at the right depth, or whether the ultrasound window is too poor for appreciating blood flow at all. Proper location and orientation of the Doppler ultrasound probe, and the proper setting of depth parameters, is typically by trial and error. Not only does this make the use of Doppler ultrasound equipment quite inconvenient and difficult, it also creates a risk that the desired sample volume may not be properly located, with the corresponding diagnosis then being untenable or potentially improper.

Once blood flow has been located, it is usually scanned along the course of the vasculature to determine if there are any localized regions in which there are flow abnormalities, which may indicate various diseases. The spectrogram is typically observed for hemodynamic clues indicating disease. However, in conventional Doppler ultrasound systems, regions having abnormal flow may be displayed ambiguously. For example, in some cases, jagged black regions, which may be construed as regions of no detected blood flow, may appear in regions where actual blood flow is indeed present. Additionally, blood flow information for regions having hemodynamic parameters of interest may be displayed in a spectrogram with aliased spectral velocities and with high-amplitude, low velocity clutter signals. The result is a spectrogram indicating blood flow velocities that "wrap around" through a maximum velocity to appear as a negative velocity along velocity axis. Both the aliased velocities and the clutter signals can severely compromise detection of peak blood flow velocity and other hemodynamic parameters.

The previously described issues with conventional Doppler ultrasound systems are often due to artifacts resulting from Doppler signal processing. A possible cause of artifacts is the presence of a bruit signal that often accompanies the pathological condition of vasospasm, a condition that results in a constriction of the vessel lumen and results in high velocity blood flow.

A bruit is a signal that appears on a Doppler spectrogram due to periodic tissue motion having a frequency in the audio range and an excursion distance of less than a wavelength of the ultrasound. In the case of a Doppler carrier frequency of 2 MHz, the wavelength is less than 780 μm. A bruit can easily be much larger in amplitude than the blood flow also present in the Doppler sample volume. For example, the detected power in a bruit signal can easily exceed that in the blood flow by 30 dB. Moreover, a bruit can be accompanied by harmonics that fall off quickly in amplitude, and by definition, bruit signals lack a directional component. The bruit is also generally significantly lower in its Doppler shift than the associated blood flow. These characteristics of bruits imply that the mean velocity estimate for the motion in the Doppler sample volume can be severely biased downward. In conventional Doppler ultrasound systems, the downward biasing will cause black regions to be displayed in regions where normal blood flow is detected since signals that have associated velocity below a clutter threshold are automatically colored black. One remedy for bruit signals is to calculate mean velocity in the spectral domain and exclude the low velocity territory where bruits tend to be present. This approach however is time consuming in that it requires a Fourier transform to be computed at every analyzed depth Another potential cause of artifacts is high velocity aliasing due to the Doppler shift frequency of detected blood flow exceeding the Nyquist frequency of the Doppler ultrasound system, the result of which is to bias the detected mean velocity to zero. The biasing is potentially significant in that the high velocities in excess of the Nyquist sampling limit are interpreted as high velocities in the opposite direction of the true blood flow and act to negate any high velocity signal data in the true flow direction. Such aliasing is can be remedied by increasing the Doppler pulse repetition frequency (PRF). However, in conventional Doppler ultrasound systems, increasing the Doppler PRF comes with a tradeoff of reducing the maximum interrogation depth, which is limited by the round trip distance an ultrasound pulse can travel before a subsequent ultrasound pulse is launched by the system.

Therefore, there is a need for an Doppler ultrasound system and Doppler signal processing method for displaying regions of blood flow having a variety of possible hemodynamic parameters and indices of interest in a fashion that yields unambiguous understanding of these parameters and where they spatially arise.

SUMMARY OF THE INVENTION

One aspect of the invention provides a Doppler ultrasound system that includes an ultrasound probe that emits ultrasound signals along an ultrasound beam axis and detects reflected signals, and further includes a processor coupled to the ultrasound probe. The processor is operable to generate Doppler ultrasound data from the detected reflected signals and process the Doppler ultrasound data to calculate blood flow data for a plurality of locations along the ultrasound beam axis and for a plurality of time intervals. The blood flow data includes blood flow velocity data and detected Doppler signal power data. The processor is further operable to identify from the blood flow data locations along the ultrasound beam axis at which blood flow having a hemodynamic characteristic is present.

In another aspect of the invention the Doppler ultrasound system further includes a graphical display coupled to the processor. Blood flow which has hemodynamic properties of interest to the user is indicated on the display by special coloring at the depth locations of the blood flow. Some examples of hemodynamics of interest that may be color coded in the display are: mean or peak velocity for use in determining and characterizing local regions of stenosis or vasospasm, volume flow indices, vessel lumen area or diameter indices, indices for characterizing systolic acceleration, resistance, ejection time, vessel compliance, and indices describing stroke conditions such as the thrombolysis in brain ischemia (TIBI) transcranial Doppler flow grades.

Another aspect of the invention provides a method for processing detected reflected signals in a Doppler ultrasound system having a ultrasound transducer emitting ultrasound signals. The detected reflected signals are processed and blood flow data for a plurality of locations along an ultrasound beam axis and for a plurality of time intervals are calculated from the processed signals. Locations along the ultrasound beam axis are identified at which blood flow having a hemodynamic characteristic is present from the calculated blood flow data. Blood flow information representative of detected blood flow and the presence of the hemodynamic characteristic is generated from the blood flow data.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of necessary fee.

FIGS. 9–12 are process flow charts depicting particular operations performed by the pulse Doppler signal processing circuitry of FIGS. 7 and 8.

DETAILED DESCRIPTION OF THE INVENTION

The following describes a method and apparatus for providing Doppler ultrasound information to a user, such as in connection with measuring blood velocities to quickly detect hemodynamically significant deviations from normal values across a range of depth. Certain details are set forth to provide a sufficient understanding of the invention. However, it will be clear to one skilled in the art that the invention may be practiced without these particular details. In other instances, well-known circuits, control signals, timing protocols, and software operations have not been shown in detail in order to avoid unnecessarily obscuring the invention.

Figure 1A:
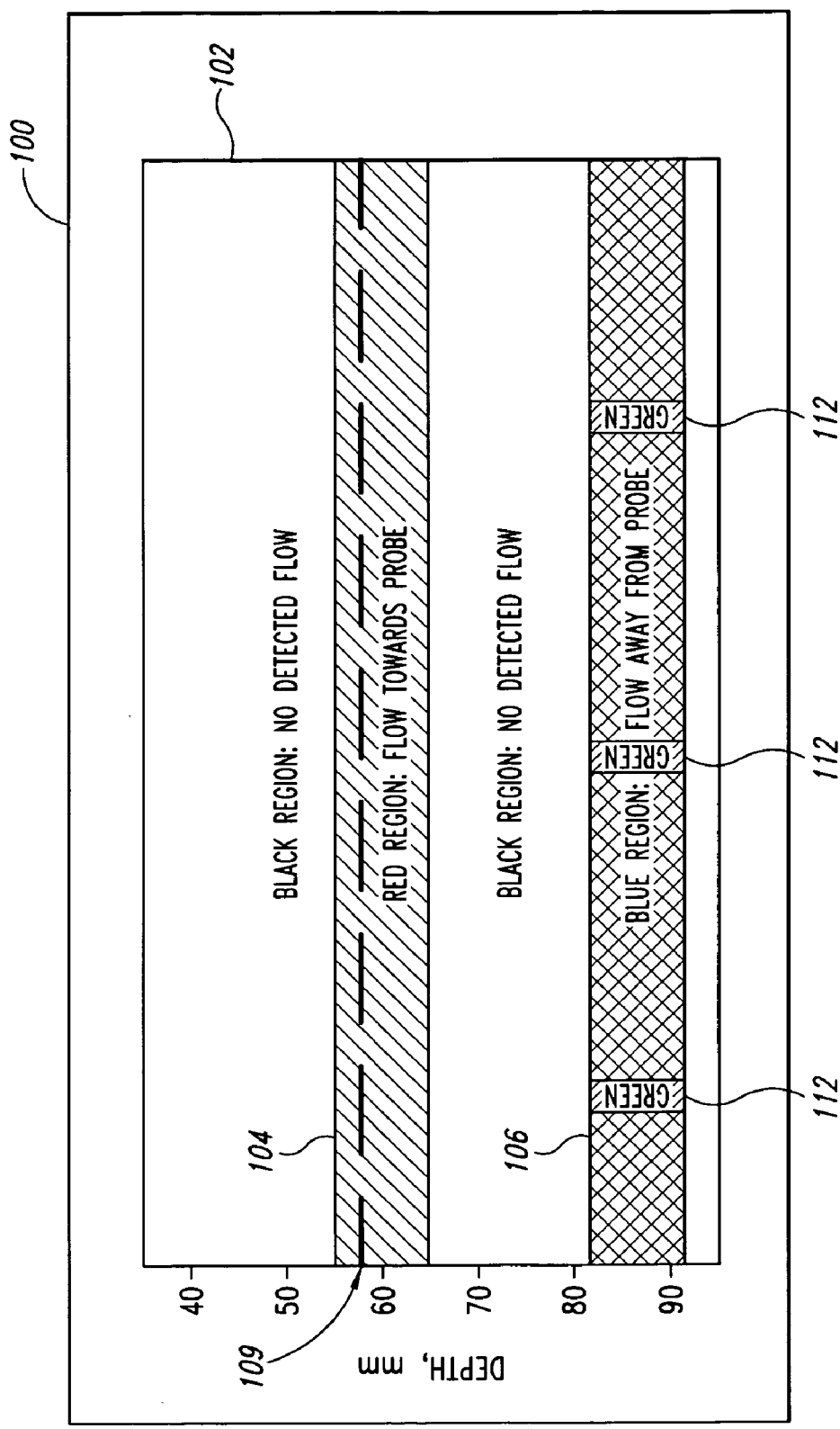
FIG. 1A is a graphical diagram depicting a Doppler ultrasound system display in accordance with an embodiment of the invention.

FIG. 1A is an Aiming Mode Display 100 depicting a display mode of Doppler ultrasound information in accordance with an embodiment of the invention. In this display mode, as shown on the Aiming Mode Display 100, a depth-mode display 102 depicts, with color, blood flow away from and towards the ultrasound probe at various depths along the ultrasound beam axis (vertical axis) as a function of time (horizontal axis). The depth-mode display 102 includes colored regions 104 and 106. Region 104 is generally colored red and depicts blood flow having a velocity component directed towards the probe and in a specific depth range. Region 106 is generally colored blue and depicts blood flow having a velocity component away from the probe and in a specific depth range. The red and blue regions are not of uniform color, but have an intensity that varies as a function of the detected intensity of the return Doppler ultrasound signal. Those skilled in the art will understand that such a display is similar to the conventional color M-mode display, in which variation in red and blue coloration is associated with variation in detected blood flow velocities. Those ordinarily skilled in the art will appreciate that properties of color other than intensity might also be employed to indicate variations in velocity and power, such as hue, saturation, and the like.

Figure 1B:
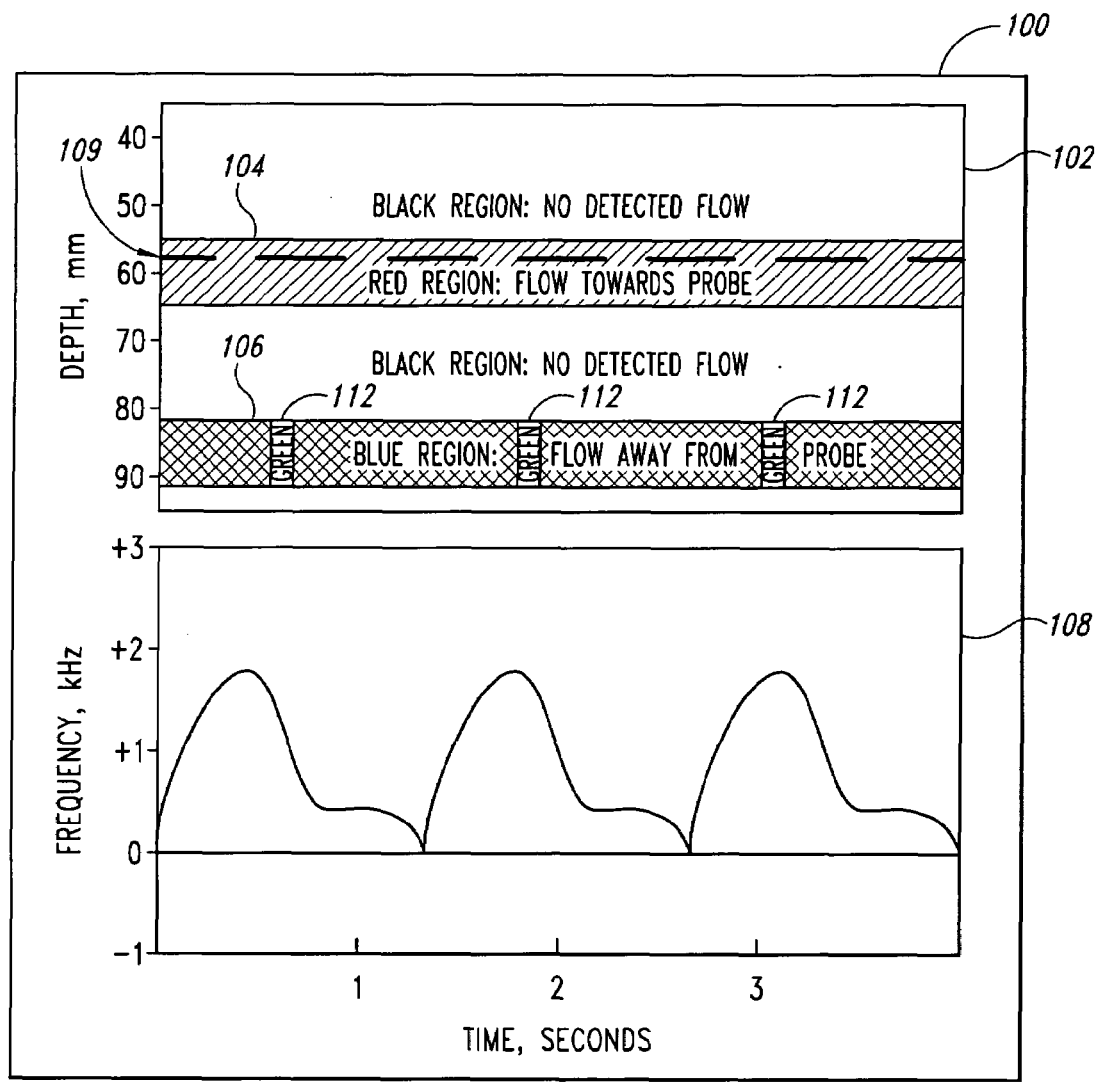
FIG. 1B is a graphical diagram depicting a Doppler ultrasound system display in accordance with an alternative embodiment of the present invention.

FIG. 1B illustrates an Aiming Mode Display 200 in which a spectrogram 108 is displayed concurrently with the depth-mode display 102. The spectrogram 108 depicts a velocity envelope showing the characteristic systolic-diastolic pattern. Like the depth-mode display 102, the spectrogram 108 includes data points (not shown) within the velocity envelope that are colored in varying intensity as a function of the detected intensity of the return ultrasound signal. The particular sample volume for which the spectrogram 108 applies is at a depth indicated in the depth-mode display 102 by a depth indicator or pointer 109. In this way, a user of the ultrasound system can conveniently see and select particular depths at which to measure the spectrogram 108.

Further included in the depth mode display 102 are colored regions 112 that represent blood flow with a particular hemodynamic property. The colored regions 112 preferably have a color that differentiates blood flow having the hemodynamic property from regions that do not, which as previously mentioned are colored either red or blue in the present embodiment. The colored regions 112 are use to indicate hemodynamic parameters in their normal ranges or hemodynamic parameters in abnormal ranges. The color regions 112 can further have a color property, such as hue, saturation, or brightness, that can be used to illustrate a magnitude of the hemodynamic property. Examples of hemodynamic parameters include, but are not restricted to: mean or peak velocity for use in determining and characterizing local regions of stenosis or vasospasm, volume flow indices, vessel lumen area or diameter indices, indices for characterizing systolic acceleration, resistance, ejection time, vessel compliance, and indices describing stroke conditions such as the thrombolysis in brain ischemia (TIBI) transcranial Doppler flow grades.

Some hemodynamic parameters have instantaneous values and vary on a continuum. Examples of this are mean or peak blood flow velocity at any given time for a blood volume contained in the Doppler sample volume, or the variance of blood flow velocity within the same sample volume. These values can be sampled and reported using time increments that are hard for the human observer to discern, such as the 100–150 lines per second sweep rate accomplished by many Doppler ultrasound devices. At 125 lines per second, there is an evaluation period of 8 milliseconds during which 64 pulses of the Doppler pulsing at 8000 times per second can be acquired and processed. Other hemodynamic parameters require a much longer and less arbitrary time period from which to calculate a value. This time period is on the order of one heart cycle and is generally 1 heart cycle per second. Indices for characterizing systolic acceleration, resistance, ejection time, vessel compliance, and TIBI flow grades should be determined from one heart cycle's worth of information to produce acceptable results. For example, calculation of the acceleration of the heart, if done on data acquired during passive filling of the heart with blood, is inaccurate because the time interval during which the heart is pumping blood in with accelerating speed has not been captured. Volume flow and vessel cross sectional area indices also require a relatively lengthy time interval to make an accurate calculation, that is, typically on the order of 10 seconds. In this case, many cycles of the heart contribute to the resulting value. All of these values which benefit from a longer interval than a fraction of a heart cycle to calculate can be calculated in an overlapping window fashion such that with every heart beat there is a new value to update the display. These indices may therefore show up on the M-mode display, as an alternate color, with persistence that lasts for a full heart cycle or multiple full heart cycles before they disappear.

The invention described here does not generally display an alternative color for every calculation of a hemodynamic parameter value, but typically when the value falls into a region of specific interest. When the systolic wave form becomes blunted, for example, during vessel blockage due to stroke, there is great interest in the acute phase of the event to quickly assess where the abnormal wave form exists in the vasculature. Therefore, displaying a continuum of coloration through the vasculature is not deemed as useful as showing an alternate color when the hemodynamic parameter moves into a range where clinical management of the patient is affected. This non-continuum system of coloring the m-mode display is termed here as a "discretized" or "binary" coloring rule and provides a benefit not found in conventional ultrasound systems.

In the embodiment shown in FIG. 1A, the color regions 112 are indicated as having a green color, and the hemodynamic parameter represented by the color regions 112 is mean blood flow velocity as a function of time that exceeds a user-set velocity threshold.

The depth-mode display 102 readily and conveniently provides the information concerning the range of appropriate depths at which a meaningful spectrogram may be obtained, for both normal and abnormal blood flow. The colored regions 112, which as previously discussed are indicative of blood flow having particular hemodynamic parameters, are meant to present the user both a screening tool and a guide by which to determine the presence of particular blood flow properties, and then help the user to quickly navigate to where the blood flow properties exist. The "navigation" here includes changing the spectrogram gate depth through the use of the depth indicator 109 in the Aiming Mode Display 200 to reside where the particular blood flow properties exist, so that this particular blood flow at the selected depth can be observed and characterized in greater detail with the spectrogram 108.

Those skilled in the art will appreciate that the diagnostic information shown in the Aiming Mode Displays 100, 200 provide advantages over conventional Power M-mode devices. While use of the spectrogram 108 is known, conventional Doppler ultrasound systems lack the ability to summarize hemodynamic parameters in a way that can be displayed on top of or concurrent with power or velocity color imaging, as provided by embodiments of the present invention. This capability will help the user navigate to regions of hemodynamic interest or monitor them in over the course of a therapy, such as for thrombolysis for acute stroke or cardiopulmonary bypass during heart surgery.

Figure 2:
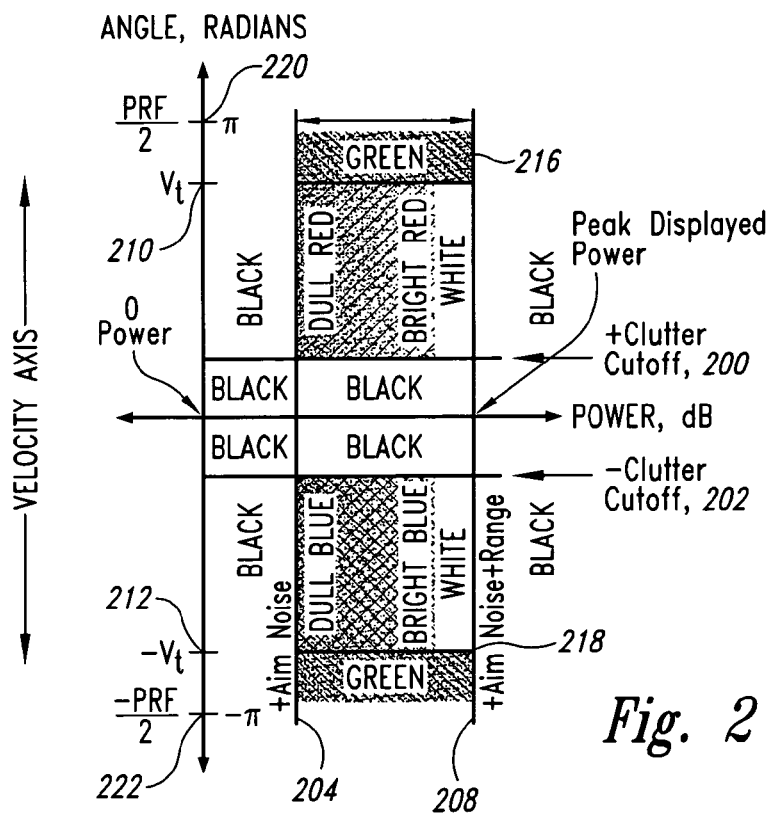
FIG. 2 is a graphical diagram depicting velocity and signal power parameters used in preparation of the display of FIGS. 1A and 1B.

As described above, the color intensity of regions 104, 106 preferably vary as a function of the detected intensity of the return ultrasound signal and the presence of the color regions 112 indicates whether a particular hemodynamic parameter is present. Referring to FIG. 2, a graphical diagram depicts how the coloring for the Aiming Mode Displays 100, 200 (FIGS. 1A, 1B) involving one example embodiment utilizing mean velocity is determined. More specifically, in order to avoid display of spurious information, signals that may be intense but low velocity (e.g., such as due to tissue motion) are ignored or filtered away and not displayed in the depth-mode display 102 of FIGS. 1A and 1B. This is referred to as clutter filtering and is depicted in FIG. 2 as the threshold magnitude clutter cutoff limits for positive and negative velocities 200, 202, respectively. Clutter filtering can assist when bruits (i.e., vessel wall vibrations that are detected as motion by the Doppler) are present. Similarly, low power signals typically associated with noise which fall below a noise threshold 204 are also ignored and not displayed in the depth-mode display 102 of FIG. 1. The user can determine an upper power limit 208 for the color intensity mapping by selecting a power range value. Signals above a maximum power are then ignored—another clutter filtering which is especially helpful when monitoring blood flow in the cardiac environment. Those skilled in the art will appreciate that other filtering techniques may be employed to improve the depth-mode display image, including delta modulator or other suitably adapted filtering techniques.

Figure 3:
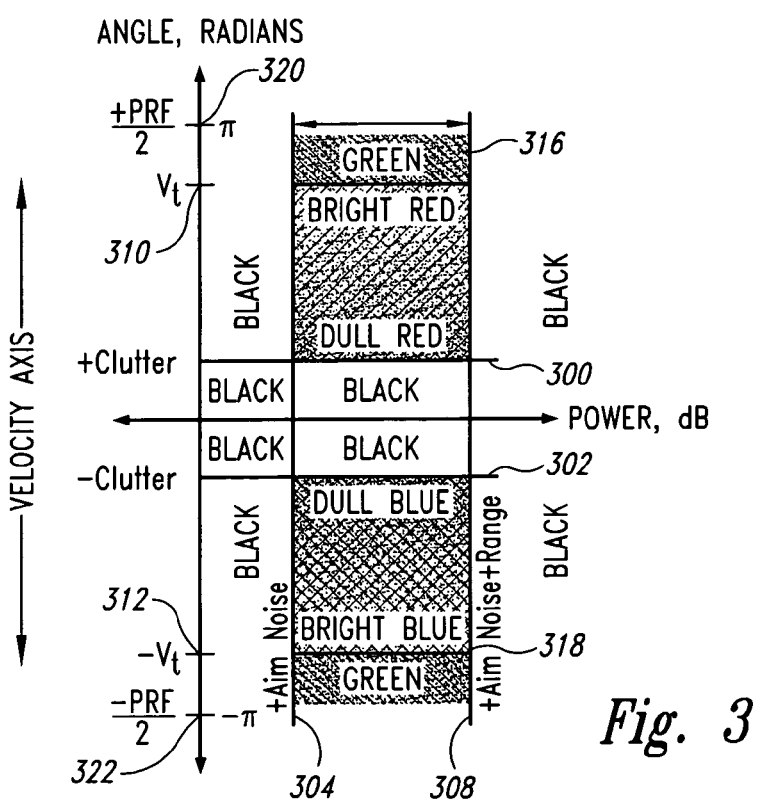
FIG. 3 is a graphical diagram depicting velocity and signal power parameters used in preparation of an alternative embodiment of the display of FIGS. 1A and 1B.

While the currently preferred embodiment of the depth-mode display 102 employs color intensity mapping for normal flow signals as a function of signal intensity, and further colored red or blue according to flow directions towards or away from the probe, those skilled in the art will appreciate that color intensity as a function of detected velocity may be employed instead. In such case, and as shown in FIG. 3, color intensity varies from the clutter cutoff magnitudes 300, 302 to a positive and negative velocity threshold Vt 310, 312, respectively. The Vt 310, 312 can be set by a user or alternatively set to an automatically selected threshold value. As described with respect to FIG. 2, in FIG. 3 detected signals having a power below the noise threshold 304 or above the selected upper power limit 308 are ignored.

Also shown in FIGS. 2 and 3 is a region between the velocity threshold Vt (210, 212 and 310, 312) and a peak velocity 220, 222 (FIG. 2) and 320, 322 (FIG. 3). The peak velocity corresponds with one-half the pulse repetition frequency (PRF). Detected signals indicative of mean blood flow velocities in excess of Vt (210, 212 and 310, 312) but less than the peak velocity (220, 222 and 320, 322) will be displayed as a function of time in the Aiming Mode Displays 100, 200 as colored regions 112. As indicated in FIGS. 2 and 3, detected signals falling within the regions (216, 218 and 316, 318) between Vt (210, 212 and 310, 312) and the peak velocity will appear as green color regions on the Aiming Mode Displays 100, 200. As previously discussed, the color regions 112 in the Aiming Mode Displays 100, 200 can be advantageously used to depict detection of abnormal blood flow velocities.

Figure 4A:
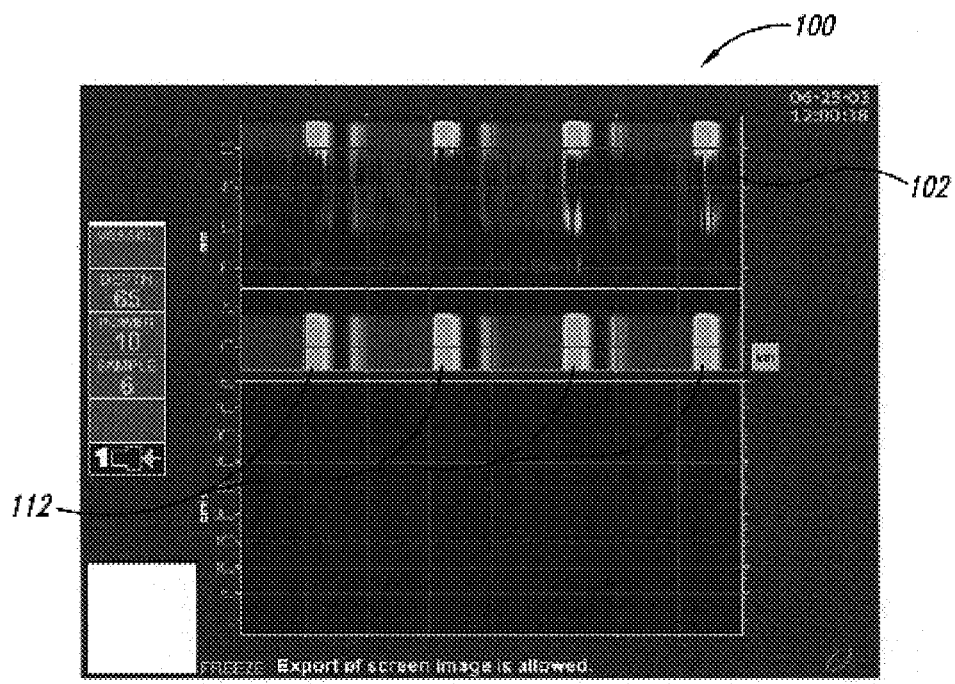
FIG. 4 shows the alternative embodiment of the display of FIGS. 1A and 1B in color.
Figure 4B:
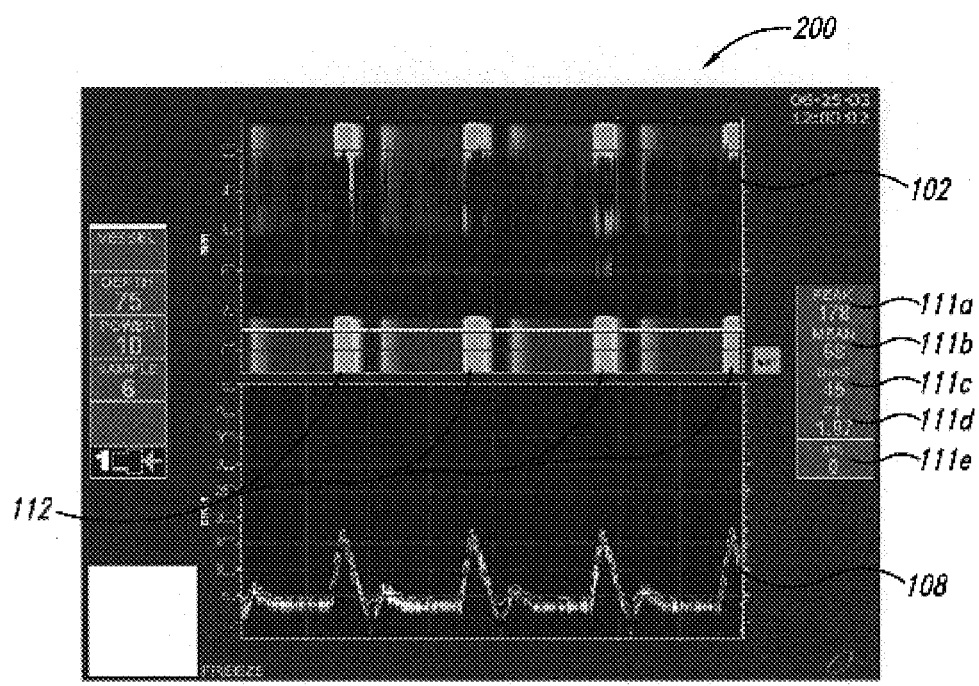

FIGS. 4A and 4B are color figures that show the Aiming Mode Displays 100, 200, respectively, in which the color intensity of the regions 104 and 106 vary as a function of detected velocity. In FIG. 4B, both the depth-mode display 102 and the spectrogram 108 are displayed relative to the same time axis, and the depth-mode display 102 shows variation both in spatial extent and in color intensity with the same periodicity as the heart beat. The green coloring of the color regions 112, which show up in this case during systole for selected regions, illustrate how the mean velocity varies with time and the blood flow of interest may be a periodic rather than a continuous presence in the Aiming Mode Display 200. Those skilled in the art will also appreciate that instead of varying color intensity in discrete regions in the power-velocity plane as depicted in FIGS. 2 and 3, one could advantageously vary color intensity as a continuous function of both signal amplitude and velocity.

The Aiming Mode Displays 100, 200 enable the user to quickly position the ultrasound probe, such as adjacent to an ultrasound window through the skull so that intracranial blood flow can be detected. Use of colorized representation of signal amplitude is particularly advantageous for this purpose, since a strong signal is indicative of good probe location and orientation. However, the use of colorized representation of flow velocity may not be as advantageous in normal or low flow signals, because the signal intensity can drop away in regions of low velocity, and therefore, be unhelpful for locating blood flow.

The Aiming Mode Display 200 also indicates to the user where to set the depth of the pulse Doppler sample gate so that the spectrogram 108 (FIG. 4B) will process Doppler shifts from desired blood flow signals. The color regions 112 indicating hemodynamic parameters of interest will be especially useful in showing the user where to set the spectrogram gate depth for more detailed analysis. The spectrogram 108 allows the user to observe and measure parameters associated with a particular blood flow and provides information that might suggest hemodynamically significant deviations in that blood flow. Along with the depth-mode display 102 and the correspondingly selected spectrogram 108, the information displayed to a user can also include well-known numerical parameters associated with the spectrogram 108, such as the mean of the peak systolic velocity 111$a$, the mean of the end diastolic velocity 111$b$ and 111$c$, pulsatility index 111$d$, and the relative change in the mean of the peak systolic velocity over time 111$e$. Those skilled in the art will appreciate that other parameters and displays may also be provided, including data provided by other monitoring devices, such as EKG- or EEG-related information.

In the previously discussed embodiments, a spectrogram for a depth selected by the depth indicator could be included with the Aiming Mode Display. It will be appreciated, however, that embodiments of the present invention could alternatively display multiple spectrograms along with the Aiming Mode Display. Selection of the depths for the spectrograms could be made through the use of separate depth indicators, which could be displayed in the Aiming Mode Display. Additionally, the previously described embodiments use a graphical display to convey blood flow information to a user. However, in alternative embodiments of the present invention, alternative user interfaces are used in place of, or in addition to a graphical display, such as audio output or LED light source. For example, audio feedback can be used to indicate the detection of an abnormal hemodynamic property, or provide the relative magnitude or level of blood flow through the use of an audible tone that changes pitch with a parameter of interest. Such audio feedback can be used instead of a graphical display of blood flow information, or in addition to the graphical display. Such modifications are well within the understanding of those ordinarily skilled in the art, and the description provided herein is sufficient to enable those so skilled to practice the present invention.

As previously discussed with respect to conventional Doppler ultrasound systems, artifacts in displaying blood flow information can result for various reasons. One reason is the presence of bruit signals, and another reason is the detection of blood flow velocities in excess of the Nyquist frequency for the Doppler ultrasound system.

A solution presented by embodiments of the present invention with respect to the presence of bruit signals is to high pass filter the Doppler signal and thereby capitalize on the difference between the Doppler shift associated with a bruit and that for blood flow. The subsequent time domain analysis of mean velocity, for example, through calculation of first-lag autocorrelation of the Doppler shift signal, will thus happen on a signal that has been scrubbed of high amplitude bruits. Normal blood flow in transcranial Doppler will generally be separated from tissue motions by setting a high pass filter cutoff to about 7 cm/s blood flow (i.e., 200 Hz for 2 MHz Doppler carrier frequency). However, embodiments of the present invention provide for setting the high pass filter cutoff at a value in excess of 7 cm/s. For example, one embodiment provides the capability of setting the high pass cutoff to up to 2.4 kHz or about 80 cm/s blood flow. It will be appreciated that the resulting blood flow velocity is in the high end of normal flow velocities, but on the low end of abnormally high flow velocities.

As also previously discussed, aliased spectral velocities resulting from blood flow velocities exceeding the Nyquist frequency can also cause artifacts. Such aliasing can be remedied by increasing the Doppler PRF. However, increasing the Doppler PRF typically comes with a tradeoff of reducing the maximum interrogation depth because it is limited by the round trip distance an ultrasound pulse can travel before a subsequent ultrasound pulse is launched by the system. That is, the "depth" parameter in medical pulse Doppler instrumentation presently available is largely determined by the formula D=ct/2, where c is the speed of sound in tissue (i.e., approximately 154,000 cm/s) and t is the time since the ultrasound pulse was launched. The factor of two accounts for t being a round trip time measurement. The value D can be further refined by the time duration of the transmitted burst, but this is typically a small fraction of the ct/2 formulation. The value D is also bounded by the Doppler pulse period, T, in order to artificially mask any ambiguity regarding echoes that come from depths beyond cT/2.

In contrast, in embodiments of the present invention, higher Doppler PRFs are used in conjunction with a lower Doppler PRF to sort out and characterize depth and severity of a high velocity signal. Thus, unlike conventional Doppler ultrasound systems, it is not necessary with embodiments of the present invention to compromise between having high PRFs to investigate high flow velocities and having adequate interrogation depth.

Figures 5A, 5B:
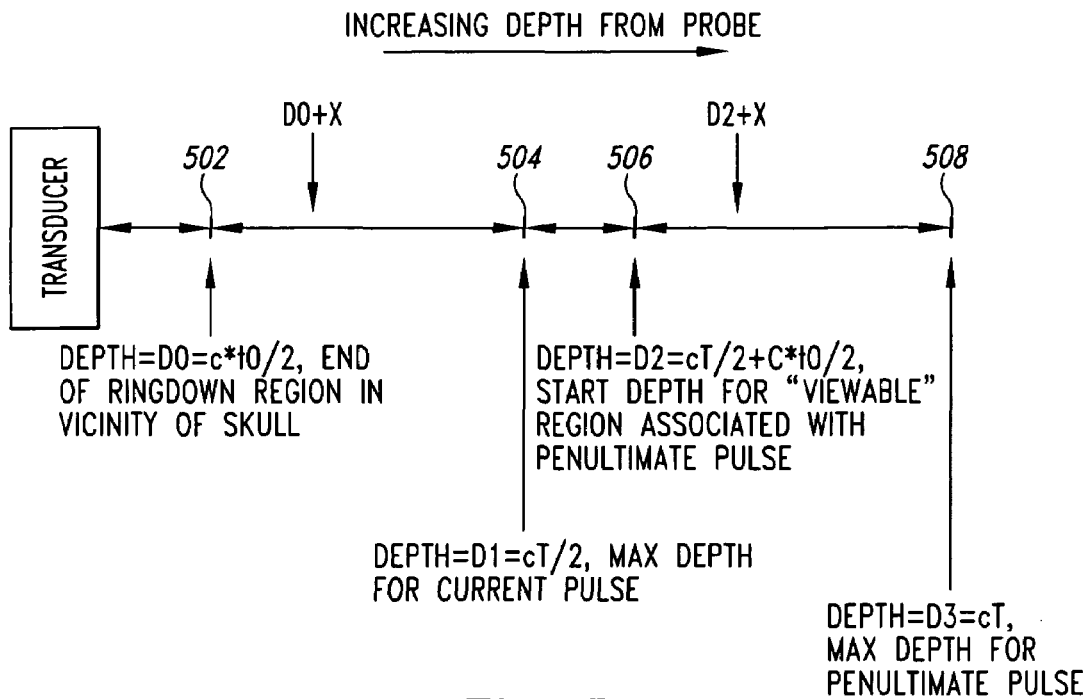
FIG. 5A is depiction of depth ranges regarding acoustic reflections from ambiguous depths.
FIG. 5B is a table showing depth ranges for various PRFs in connection with FIG. 5A.

FIGS. 5A and 5B have been provided to help describe high velocity detection in embodiments of the present invention. FIG. 5A depicts depth ranges associated with acoustic reflections in the context of those from the "current" pulse and those from the previous or penultimate pulse. There are four depths of interest in FIG. 5A. Depth D0 502 marks the end of a depth range adjacent to the ultrasound transducer that is associated with the transducer being active and the time period immediately afterward when there are large echoes returning from skull tissue. That is, the Doppler signal between depths of 0 and D0 502 is undecipherable. D0 502 is shown as 11 mm in FIG. 5A. A depth of 11 mm is shown as a conservative worst case scenario. However, it will be appreciated that D0 502 is independent of the Doppler PRF and will be different with different transmit burst lengths, skull reflection properties and receiver processing circuitry.

A depth D1 504 marks the end of the "normal" depth range associated with the pulse repetition frequency (cT/2 where T is time between outgoing pulses). A depth D2 506 is the start of the decipherable depth range associated with the penultimate Doppler pulse. There is therefore a gap in "viewable" tissue between D1 and D2. A depth D3 508 marks the end of the depth range associated with the penultimate pulse of the Doppler. Reflections arising from tissue between D2 and D3 arrive and are interpreted as reflections from tissue between D0 and D1. The "ambiguous depth" D2+X is contributing to signals interpreted from depth D0+X, where X is an arbitrary distance less than D1-D0.

At 8 kHz PRF as shown in the first row of the table in FIG. 5B, D1=96 mm is more than half the width of the head of a patient, which places D1 504 in the contralateral portion of the brain. Reflections from the region between D2 and D3 are generally quite weak compared to those between D0 and D1, due to tissue attenuation and lateral spread of the ultrasound beam. These are not considered to produce ambiguous flow signals in standard transcranial Doppler. However, the situation is not the same when considering higher PRFs, such as 12.5 kHz and 15.625 kHz, and must be taken into account in exploration of high velocity signals on the Aiming Mode Displays 100, 200.

At a PRF of 12.5 kHz, an anterior cerebral artery signal at 75 mm depth (i.e., D2=72 mm, X=3 mm) will alias to D0+X=14 mm depth where there may be a complete absence of flow as seen with 8 kHz PRF. Similarly, at a 15.625 kHz PRF, an anterior cerebral artery signal at 75 mm depth (i.e., D2=60 mm, X=15 mm) will alias to D0+X=26 mm depth where there may or may not be flow detected with 8 kHz PRF. This situation illustrates the need to sort out the context of the flow signals at the lower PRF in order to verify the position of a high velocity flow signal as seen at the higher PRFs.

Sorting out and characterizing depth and severity of a high velocity signal can be accomplished by the ultrasound technologist exploring for pathological signals at the higher PRFs (e.g., 12.5 kHz and 15.625 kHz) and high clutter filter settings, but doing so with reference to where flow signals are detected at the lower PRF of 8 kHz. At the lower frequency PRF high velocities will usually appear bracketed in a region of normal looking flow (red or blue). The high velocities with the normal margins is often blacked out in appearance and jagged on the edges, but the depth at which this characteristic appearance presents is the true location of the pathology. If the user positions the sample gate into this region and then switches to high PRF to characterize the high velocities in their spatial extent and severity, the system will map the signals of interest to either the D0-D1 region or the D2-D3 region and the correct spatial depths for the signals of interest is maintained.

Note that the D1-D2 gap of flow information illustrated in FIG. 5 occurs at a different place for 12.5 kHz compared to 15.625 kHz. This means that the high velocities which reside in the "gap" region for one PRF can be nevertheless observed with the second PRF. Maximum velocities in vasospasm and stenosis in general rarely exceed 480 cm/s. As a result, both of the high PRFs are capable of characterizing peak stenotic velocities with the spectrogram 108. The resulting image displayed on the Aiming Mode Displays 100, 200 for the different high PRFs will each have a region where no flow signals appear, as illustrated in FIG. 4.

One skilled in the art will appreciate that if there are multiple blood flow signals mapped to one depth location as described above and depicted in FIG. 5, the spectrogram 108 will present a signal where the vasospasm severity is not masked unless vasospasm is concurrently located in two places separated by a distance D1 504, and both locations are aligned in the ultrasound beam simultaneously. However, this scenario is considered to have a very low probability of occurring.

Figure 6:
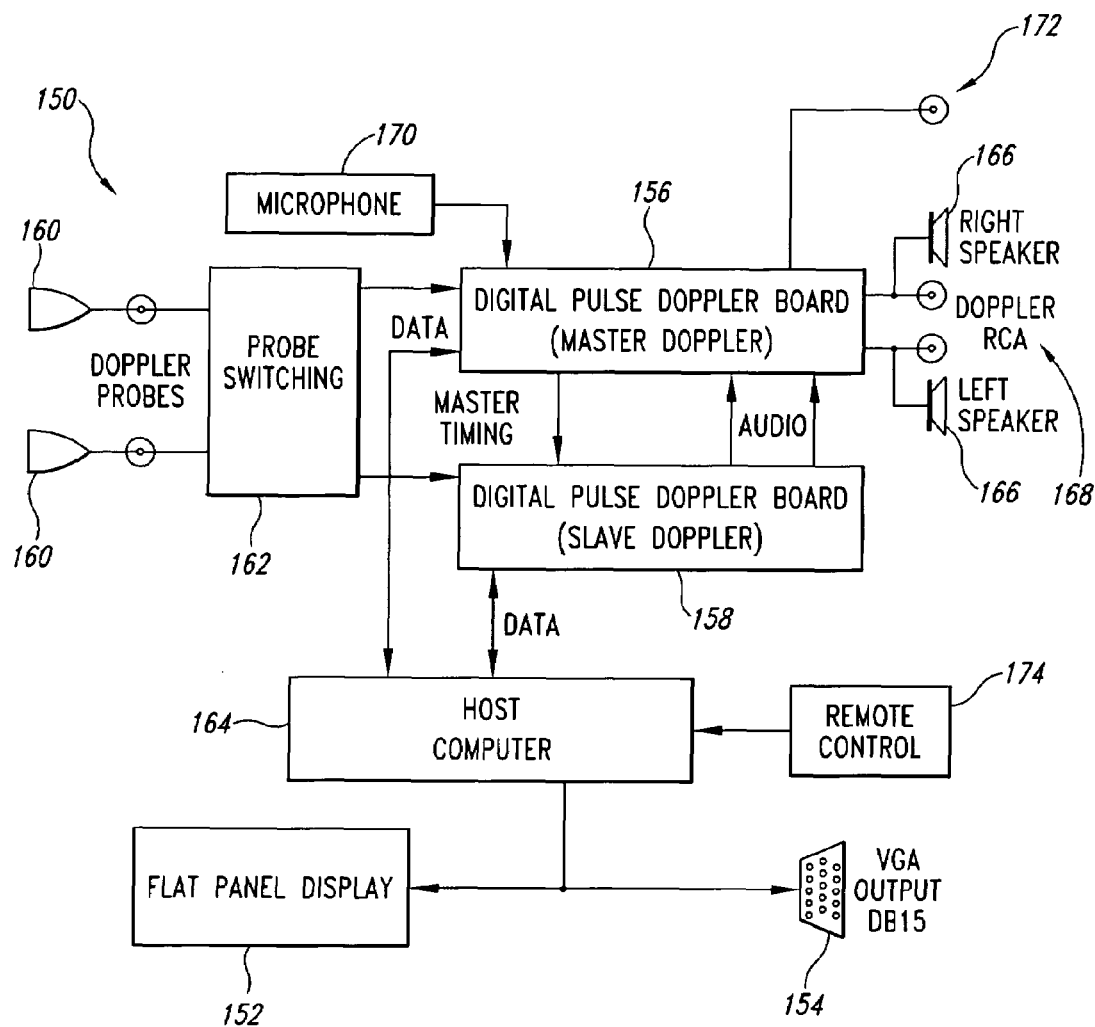
FIG. 6 is a functional block diagram depicting a Doppler ultrasound system in accordance with an embodiment of the invention.

FIG. 6 is a functional block diagram that depicts an ultrasound system 150 in accordance with an embodiment of the invention. The ultrasound system 150 produces the various display modes described above in connection with FIGS. 1–5 on an integrated flat panel display 152 or other desired display format via a display interface connector 154. The signal processing core of the Doppler ultrasound system 150 is a master pulse Doppler circuit 156 and a slave pulse Doppler circuit 158. The Doppler probes 160 are coupled with other system components by a probe switching circuit 162. The probe switching circuit 162 provides both presence-detect functionality and the ability to distinguish between various probes, such as by detecting encoding resistors used in probe cables or by other conventional probe-type detection. By providing both the master and slave pulse Doppler circuits 156 and 158, two separate ultrasound probes 160 may be employed, thereby providing unilateral or bilateral ultrasound sensing capability (such as bilateral transcranial measurement of blood velocity in the basal arteries of the brain). The master and slave pulse Doppler circuits 156 and 158 receive the ultrasound signals detected by the respective probes 160 and perform signal and data processing operations, as will be described in detail below. Data is then transmitted to a general purpose host computer 164 that provides data storage and display. A suitable host computer 164 is a 200 MHz Pentium processor-based system having display, keyboard, internal hard disk, and external storage controllers, although any of a variety of suitably adapted computer systems may be employed.

The ultrasound system 150 also provides Doppler audio output signals via audio speakers 166, as well as via audio lines 168 for storage or for output via an alternative medium. The ultrasound system 150 also includes a microphone 170 for receipt of audible information input by the user. This information can then be output for external storage or playback via a voice line 172. The user interfaces with the ultrasound system 150 primarily via a keyboard or other remote input control unit 174 coupled with the host computer 164.

Figure 7:
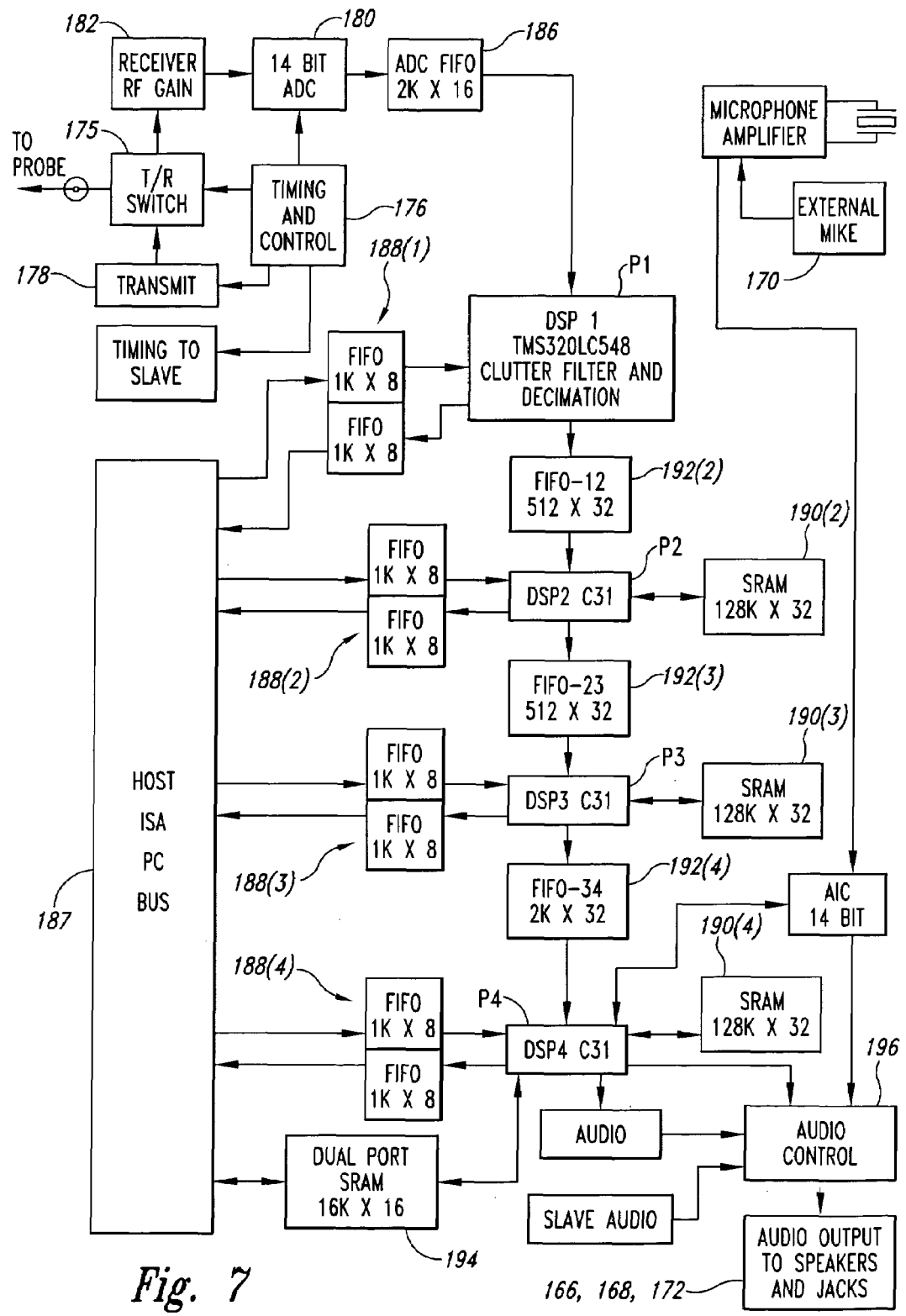
FIGS. 7 and 8 are functional block diagrams depicting particular details of pulse Doppler signal processing circuitry included in the Doppler ultrasound system of FIG. 6.
Figure 8:
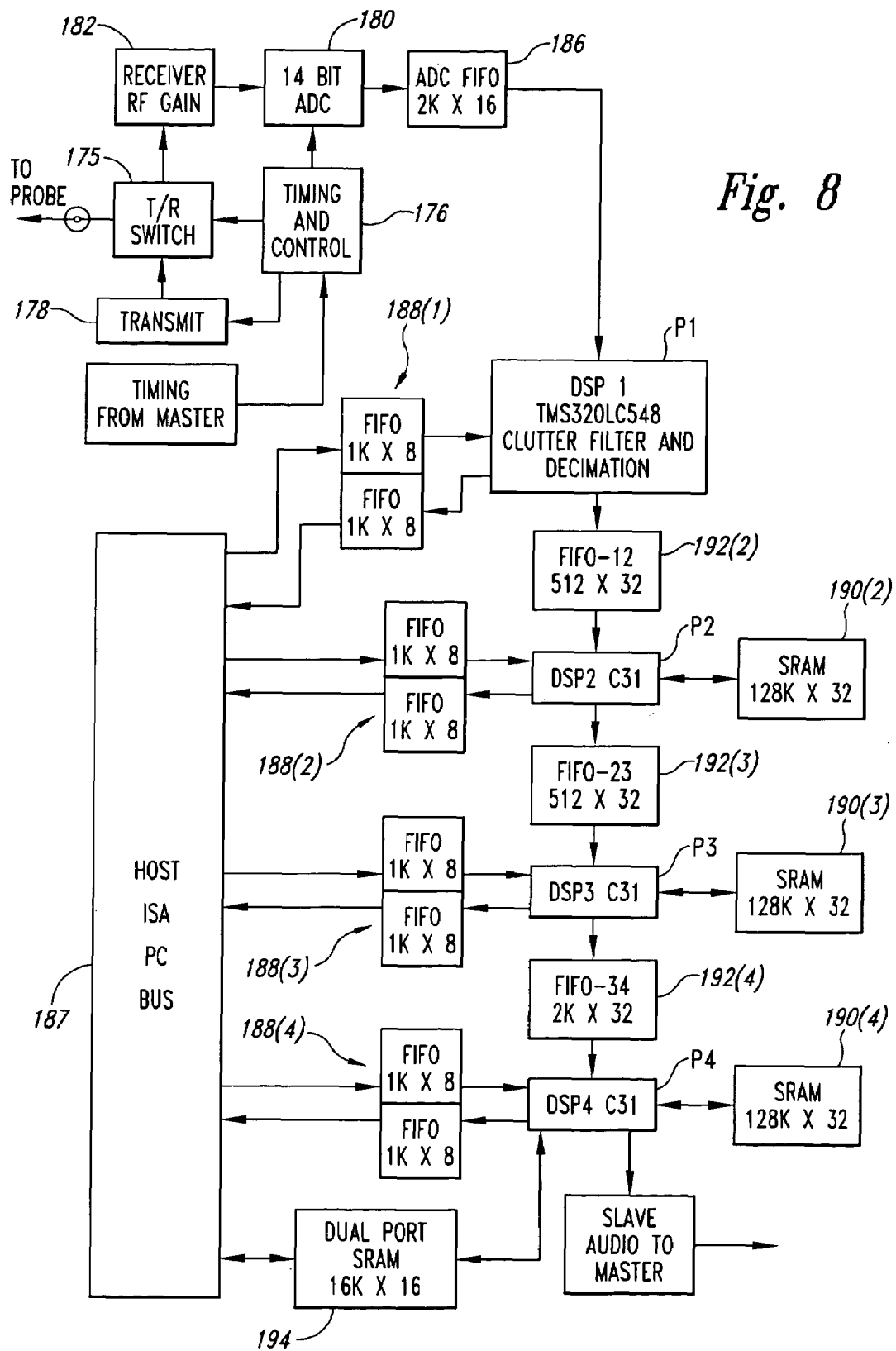

FIGS. 7 and 8 depict particular details of the master and slave pulse Doppler circuits 156 and 158. To the extent FIGS. 7 and 8 depict similar circuit structures and interconnections, these will be described once with identical reference numbers used in both Figures. FIG. 7 also depicts details concerning the input and output of audio information to and from the ultrasound system 150 via the microphone 170, the speakers 166, and the audio output lines 168 & 172, the operations of which are controlled by the master pulse Doppler circuit 156.

At the transducer input/output stage, each of the pulse Doppler circuits 156 and 158 includes a transmit/receive switch circuit 175 operating under control of a timing and control circuit 176 (with the particular timing of operations being controlled by the timing and control circuit 176 of the master pulse Doppler circuit 156). The timing and control circuit 176 also controls operation of a transmit circuit 178 that provides the output drive signal causing the Doppler probes 160 (see FIG. 6) to emit ultrasound. The timing and control circuit 176 also controls an analog-to-digital converter circuit 180 coupled to the transmit/receive switch 175 by a receiver circuit 182. The function and operation of circuits 175–182 are well known to those skilled in the art and need not be described further.

The primary signal processing functions of the pulse Doppler circuits 156 and 158 are performed by four digital signal processors P1–P4. P1 is at the front end and receives digitized transducer data from the receiver 182 via the analog-to-digital converter circuit 180 and a data buffer circuit or FIFO 186. P4 is at the back end and performs higher level tasks such as final display preparation. A suitable digital signal processor for P1 is a Texas Instruments TMS320LC549 integer processor, and suitable digital signal processors for P2–P4 are Texas Instruments TMS320C31 floating point processors, although other digital signal processing circuits may be employed to perform substantially the same functions in accordance with the invention.

Received ultrasound signals are first processed by the digital signal processor P1 and then passed through the signal processing pipeline of the digital signal processors P2, P3, and P4. As described in detail below, the digital signal processor P1 constructs quadrature vectors from the received digital data, performs filtering operations, and outputs Doppler shift signals associated with 64 different range gate positions. The digital signal processor P2 performs clutter cancellation at all gate depths. The digital signal processor P3 performs a variety of calculations, including autocorrelation, phase, and power calculations. P3 also provides preparation of the quadrature data for stereo audio output. The digital signal processor P4 performs most of the calculations associated with the spectrogram display, including computation of the spectrogram envelope, systole detection, and also prepares final calculations associated with preparation of the Aiming display.

Each of the digital signal processors P1–P4 is coupled with the host computer 164 (see FIG. 6) via a host bus 187 and control data buffer circuitry, such as corresponding FIFOs 188(1)–188(4). This buffer circuitry allows initialization and program loading of the digital signal processors P1–P4, as well as other operational communications between the digital signal processors P1–P4 and the host computer. Each of the digital signal processors P2–P4 is coupled with an associated high-speed memory or SRAM 190(2)–190(4), which function as program and data memories for the associated signal processors. In the particularly depicted signal processing chain of FIG. 7 or 8 the digital signal processor P1 has sufficient internal memory, and no external program and data memory need be provided. Transmission of data from one digital signal processor to the next is provided by intervening data buffer or FIFO circuitry 192(2)–192(4). The ultrasound data processed by the digital signal processor P4 is provided to the host computer 164 via data buffer circuitry such as a dual port SRAM 194.

Referring to FIG. 7, the digital signal processor P4 of the master pulse Doppler circuit 156 also processes audio input via the microphone 170, as well as controlling provision of the audio output signals to the speakers 166 and audio output lines 168, 172. P4 controls the audio output signals by controlling operations of an audio control circuit 196, which receives audio signals from both the master and the slave pulse Doppler circuits 156 and 158.

Referring to process flow charts shown in FIGS. 9–12, a detailed description will now be provided of the operations performed by of each of the digital signal processors P1–P4 included in both the master and slave pulse Doppler circuits 156 and 158. Particular detailed calculations and numerical information are provided to disclose a current embodiment of the invention, but those skilled in the art will appreciate that these details are exemplary and need not be included in other embodiments of the invention.

Figures 9, 10:
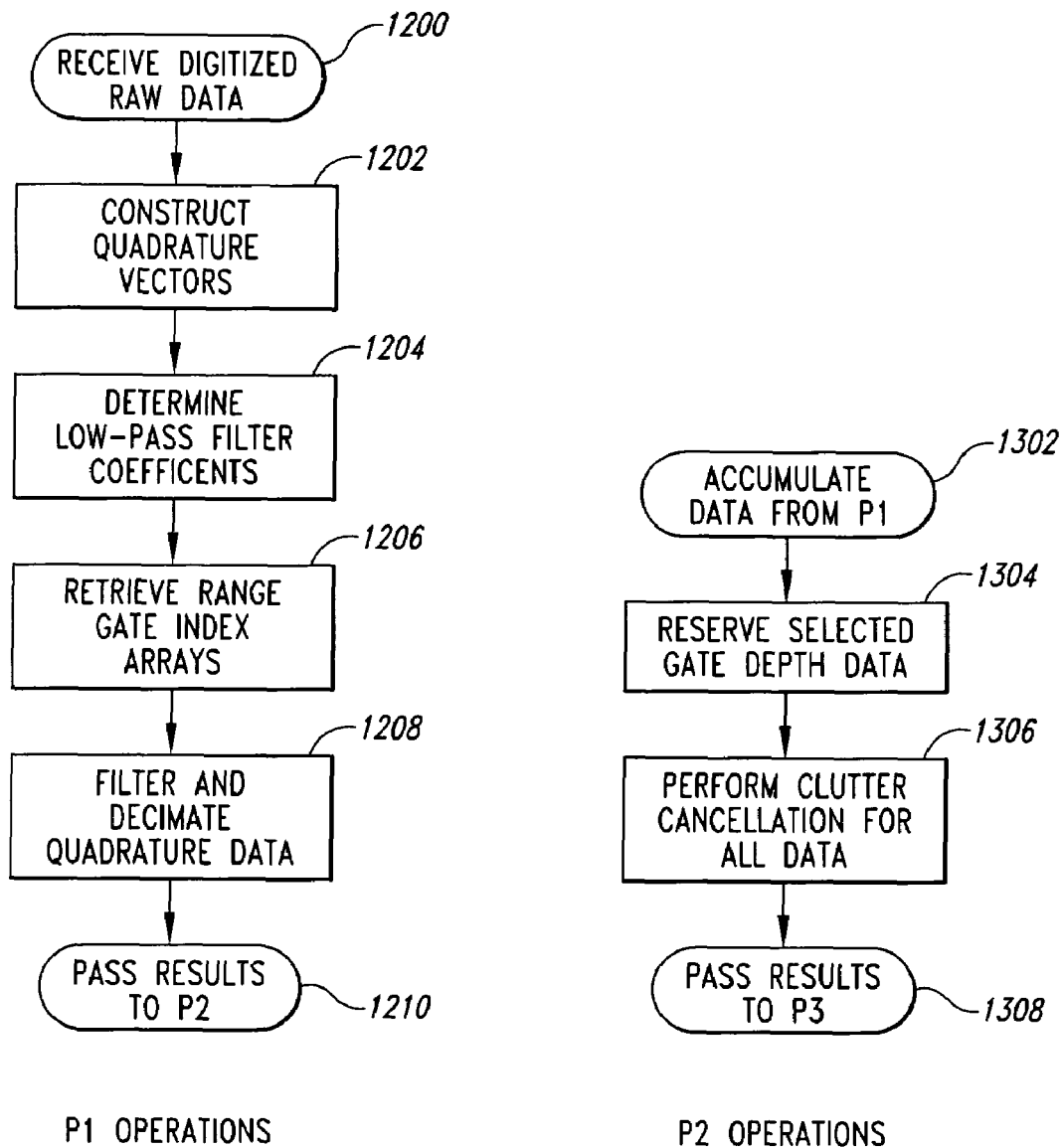

Referring to FIG. 9, the operations of digital signal processor P1 are as follows:
1. RECEIVE DIGITIZED RAW DATA 1200. Read A(1:N), a series of N 14-bit values from the input A/D. The values are converted at 4× the Doppler carrier frequency (8 MHz), and commence synchronously with the start of the transmit burst. N=1000 if the Doppler pulse repetition frequency (PRF) is 8 kHz, 1280 if the Doppler PRF is 6.25 kHz, 1600 if the Doppler PRF is 5 kHz, 640 if the PRF is 12.5 kHz, and 512 if the PRF is 15.625 kHz.
2. QUADRATURE VECTOR CONSTRUCTION 1202. Construct two vectors with N/4 points each according to the following rules: Br(1:N/4)=A(1:4:N-3)-A(3:4:N-1), and Bi(1:N/4)=A(2:4:N-2)-A(4:4:N). Br and Bi are the digitally demodulated quadrature Doppler values for a series of N/4 different gate depths. The subtractions here remove DC bias from the data.
3. LOW-PASS FILTER COEFFICIENTS 1204. Br and Bi contain frequencies up to carrier/4, and need to be further filtered to remove noise outside the bandwidth of the Doppler transmit burst. The coefficients for accomplishing this low-pass filtering are determined by a creating, with standard digital filter design software such as MATLAB, an order 21 low-pass FIR filter. The normalized cutoff of this filter is 2/(T*fs), where T is the time duration of the transmit burst, and fs is the sample rate of the data in Br and Bi (2 MHz). Call this filter C(1:21). The coefficients of this filter will vary as the transmit burst length is changed by the user, and a bank of several different sets of filter coefficients is accordingly stored to memory.

4. INDEX ARRAYS 1206. Data from 33 range gate positions are to be processed and passed to P2. It will be appreciated by those ordinarily skilled in the art that although the number of gates processed here is noted as 33, the number of gates may vary based on the desired PRF. That is, as the PRF increases, the calculation demand on the front end portion of the processing chain increases as well. For ease of graphical display, the 33 range gate positions are selected to be 1 mm apart. However, the quadrature vectors Br and Bi do not contain elements that are spaced 1 mm apart—they are 0.385 mm apart. Therefore, indices into the Br and Bi arrays are used that correspond to values falling closest to multiples of 1 mm, as a means to decimating Br and Bi to 1 mm sampling increments. This is done by having a prestored array of indices, D1(1:33), corresponding to depths 22:86 mm in 2 mm increments for 8 kHz PRF, and indices D2(1:33), D3(1:33), D4(1:20) and D5(1:12) with corresponding or deeper depth ranges for 6.25 kHz, 5 kHz, 12.5 kHz and 15.625 kHz PRFs. Higher PRF (i.e., 12.5 kHz and 15.625 kHz) depth ranges in this embodiment span the same depth range as that for 8 kHz but use fewer gates. More specifically, 20 gates are processed at 12.5 kHz and 12 gates are processed at 15.625 kHz. The spacing between gates is made larger to 3 mm, which is sufficient to cover the desired range when spatial sample volume aliasing and the "ring-down" region are considered as noted in detail earlier.

5. LOW-PASS FILTER AND DECIMATION OF QUADRATURE DATA 1208. The Br and Bi arrays are low-pass filtered and decimated to 64 gates, by the following rules (note <a,b> is the 32 bit accumulated integer dot product of vectors a and b):

8 kHz PRF:

$Er(j)=<C, Br(D1(j)+(-10:10))>$ $Ei(j)=<C, Bi(D1(j)+(-10:10))>$, and $j=1:33$. 6.25 kHz PRF:

$Er(j)=<C, Br(D2(j)+(-10:10))>$ $Ei(j)=<C, Bi(D2(j)+(-10:10))>$, and $j=1:33$. 5 kHz PRF:

$Er(j)=<C, Br(D3(j)+(-10:10))>$ $Ei(j)=<C, Bi(D3(j)+(-10:10))>$, and $j=1:33$. 12.5 kHz PRF:

$Er(j)=<C, Br(D4(j)+(-10:10))>$ $Ei(j)=<C, Bi(D4(j)+(-10:10))>$, and $j=1:20$. 15.625 kHz PRF:

$Er(j)=<C, Br(D5(j)+(-10:10))>$ $Ei(j)=<C, Bi(D5(j)+(-10:10))>$, and $j=1:12$.

6. PASS RESULTS TO P2 1210. Er and Ei, comprise the Doppler shift data for 1 pulse repetition period, over a set of different sample gates spanning the depth ranges described above. These arrays are passed to P2 with each new transmit burst.

Referring to FIG. 10, the operations of digital signal processor P2 are as follows:

1. ACCUMULATE INPUT DATA 1302. Collect a buffer of M Er and Ei vectors from P1 over a period of 8 ms, into floating point matrices Fr and Fi. At the PRFs of [8,6.25, 5,12.5,15.625] kHz, the matrices Fr and Fi will each contain respectively M=[64,50,40,100,125] vectors. The jth Er and Ei vectors at their respective destinations are denoted by Fr(1:MGATES,j) and Fi(1:MGATES,j) (these are column vectors and MGATES is the number of gates processed for the particular PRF). The kth gate depth across the M collected vectors is indexed by Fr(k,1:M) and Fi(k,1:M) (these are row vectors).

2. PRESERVATION OF RAW DATA AT "CHOSEN" GATE DEPTH 1304. Reserve in separate buffer the raw data at the user-chosen gate depth, k, at which the Doppler spectrogram is processed. This row vector data, Gr(1:M)=Fr(k,1:M) and Gi(1:M)=Fi(k,1:M), is passed forward to P3 and eventually to the host for recording purposes.

3. CLUTTER CANCELLATION 1306. Apply a fourth order clutter cancellation filter to each row of Fr and Fi. Hr(1:MGATES,1:M) and Hi(1:MGATES,1:M) are the destination matrices of the filtered Fr(1:64,1:MGATES) and Fi(1:64,1:MGATES) data. Application of this filter with continuity requires maintaining state variables and some previous Fr and Fi values. The coefficients of the clutter filter will vary depending on the PRF and the user's particular selection. In an embodiment of the present invention, the range of coefficients range from 25 Hz to 2400 Hz. These coefficients are available by table lookup in processor RAM, given the user choice from the above options.

4. PASS RESULTS TO P3 1308. Gr, Gi, Hr and Hi are passed to P3 for further processing.

Referring to FIG. 11, the operations of digital signal processor P3 are as follows:

1. ACCUMULATE INPUT DATA 1402. Receive Gr, Gi, Hr and Hi from P2.

2. COMPUTE AUTOCORRELATION 1404. Compute the first lag of the autocorrelation of the data at each gate over time. Use all M values at each gate in this calculation. This will generate an array of MGATES complex values, one for each gate. For the kth gate depth, let P=Hr(k,1:M)+jHi(k,1:M). Then the first lag autocorrelation for this depth is AC(k)=<P(1:M-1),P(2:M)>. (Note that in a dot product of complex values, the second vector is conjugated. Also note that this and all dot products in P2, P3, or P4 are floating point calculations.) In this manner, construct the complex vector AC(1:MGATES).

3. COMPUTE PHASE FOR EACH AC VALUE 1406. For each autocorrelation value, us a four quadrant arctangent lookup to determine the phase of the complex value. Specifically, ANGLE(k)=arctan(imag(AC(k) ), real(AC(k))). The ANGLE(k) value is proportional to the mean flow velocity at the gate depth k.

4. COMPUTE POWER 1408. Compute the signal power. Use all M values at each gate in this calculation. This will generate an array of MGATES real values, one for each gate. For the kth gate depth, again let P=Hr(k,1:M)+jHi(k,1:M). Then the power for this depth is POWER(k)=<P(1:M),P(1:M)>(note that in a dot product of complex values, the second vector is conjugated). In this manner, construct the real vector POWER(1:MGATES).

5. LOG COMPRESS POWER 1410. Convert POWER to Decibels: POWERd(1:MGATES)=10*log 10(POWER(1:MGATES)).

6. COMPLEX BANDPASS FILTER FOR USE IN AUDIO OUTPUT PREPARATION 1412. The min and max frequencies resulting from user specified spectral unwrapping of the spectrogram are used to determine a complex bandpass filter for making the audio output sound congruent with what is shown on the spectrogram display. For example, if the unwrapping occurs at [−1,7] kHz, then the audio complex bandpass filter has edges at −1 kHz and +7 kHz. A bank of several sets of complex bandpass filter coefficients, corresponding to different unwrap ranges, is generated offline and placed in memory. Each coefficient set corresponds to one of the unwrapping selections the user can make. Let the operative set of filter coefficients be called UWa(1:O) and UWb(1:O), where O is the filter order plus one.

7. AUDIO OUTPUT PREPARATION: RESAMPLE 1414. At the gate depth selected by the user, k, the Doppler shift signals are to be played out the audio speakers. Before doing so, some prepping of the audio signals is important to match the user-selected spectral unwrapping. Resample the audio signal Hr(k,1:M) and Hi(k,1:M) to twice the PRF by multiplexing the respective arrays with zeros: Qr(k,1:2M)={Hr(k,1), 0, Hr(k,2), 0, Hr(k,3), 0, . . . , Hr(k,M), 0} and Qi(k,1:2M)={Hi(k,1), 0, Hi(k,2), 0, Hi(k,3), 0, . . . , Hi(k,M), 0}.

8. AUDIO OUTPUT PREPARATION: COMPLEX BANDPASS 1414. Apply a complex bandpass filter to Qr+jQi in order to remove the extra images introduced by multiplexing the data with zeros:

$$R(n)=UWb(1)*Q(n)+UWb(2)*Q(n-1)+ \ldots +UWb(O)\\ *Q(n-O+1)-Uwa(2)*R(n-1)-\\ Uwa(3)*R(n-2)- \ldots -Uwa(O)*R(n-O+1)$$

where Q(k)=Qr(k)+jQi(k).

9. AUDIO OUTPUT PREPARATION: HILBERT TRANSFORM 1416. The audio data in the sequence R(n) is in quadrature format and needs to be converted into stereo left and right for playing to the operator. This is done with a Hilbert transform, and a 95 point transform, H(1:95), is used in this work—the coefficients can be obtained with formulas in the literature or standard signal processing software such as MATLAB. The application of the Hilbert transform to a data sequence is done as an FIR filter. Construction of stereo separated signals RL and RR from R(n) is done according to [RL=Hilbert(Rr)+Delay(Ri), RR=Hilbert(Rr)−Delay(Ri)] where Delay is a (Nh+1)/2 step delay of the imaginary component of R, and Nh is the size of the Hilbert filter (95).

10. PASS RESULTS TO P4, 1418. Pass Gr, Gi, ANGLE, POWERd, Rr, Ri, RL and RR to P4 for further processing. Referring to FIG. 12, the operations of digital signal processor P4 are as follows:

1. ACCUMULATE INPUT DATA 1502. Receive Gr, Gi, ANGLE, POWERd, Rr, Ri, RL and RR from P3.

2. CALCULATE SPECTROGRAM 1504. Compute power spectrum via the following steps: a) Concatenate, new points in the Rr+jRi sequence with old points such that there are 128 points altogether, b) Multiply the 128 point sequence against a 128 point Hanning window, c) Calculate P, the FFT of the 128 point sequence, d) Calculate Pd=10*log 10(P), and e) FFTSHIFT the Pd sequence such that DC is at a user-selected position.

3. ENVELOPE 1506. Compute the maximum frequency follower or "envelope" function, E(j), which indicates the upper edge of the flow signals in the spectrogram. This is a value calculated once with each new FFT calculation—i.e., for every spectral line calculation there is one value of E. Those skilled in the art will know of a variety of algorithms for making this calculation.

4. SYSTOLE DETECTION 1508. Based on the maximum frequency follower, detect the start of systole. When the systolic start has been determined, set SYSTOLE_FLAG=TRUE. Also calculate the end diastolic velocity value, VEND, the peak systolic velocity value, VPEAK, and the mean velocity, VMEAN.

5. HIGHER PRF DATA INTERPOLATION 1510. If the PRF is 12.5 kHz or 15.625 kHz, then the number of gates processed, MGATES, is less than 33. Resample this data by interpolation to obtain 33 gates, which make subsequent processing for display purposes operate uniformly on 33 gates input. In notation here, the POWERd2 and the ANGLE vectors are considered to have 33 gates each for input into the next processing step.

6. AIMING DISPLAY PREPARATION 1512. Prepare the Aiming display via the following steps: a) Subtract the value of the "aim noise" parameter set by the user from the POWERd array: POWERd2=POWERd−aim_noise, b) multiply POWERd2 by a factor which is 64 (the number of color shades) divided by the value of the "aim range" parameter set by the user—POWERd3=POWERd2*64/aim_range, c) clip the resulting power data at 0 on the low end and 63 on the high end—the values now correspond to entries in a 64-value red or blue color table, and place results in array POWERd4, and d) multiply each of the power values by 1, 0 or −1, depending respectively on whether the associated ANGLE value is greater than the "filter cutoff parameter", less in absolute value than the filter cutoff parameter, or less than the negative of the filter cutoff parameter. This results in 64 values (one per gate depth) in the range of [−64,+63]. Finally, indicate with a special reserved color code those elements where the hemodynamic parameter of interest is TRUE. For example in the embodiment illustrated in FIG. 1 with velocity threshold, if the ANGLE exceeds a preset ANGLE_THRESHold, then assign the special color code. This modified aiming array, POWERd5, is ready to display after sending to the host computer.

7. SPECTROGRAM DISPLAY PREPARATION 1514. Prepare the spectrogram display via the following steps: a) Subtract the user-selected noise floor parameter from the array Pd−Pd2=Pd-spectral_noise, b) Rescale the spectral data to contain 256 colors across the user-specified dynamic range−Pd3=Pd2*256/spectral_range, c) truncate/clip the data to be integer valued from 0 to 255−Pd4=min(255,floor(Pd3)), d) truncate the data to 8 bits−Pd5=8 bit truncate(Pd4).

8. AUDIO OUTPUT 1516. Send the arrays. RR and RL, the right and left speaker audio outputs, to the speakers via port writes.

9. INPUT MICROPHONE 1518. Sample M values into vector MIC from the input microphone port (M is # of transmit pulse repetitions within an 8 ms period).

10. PASS RESULTS TO HOST COMPUTER 1520. Pass Gr, Gi, POWERd5, Pd5, SYSTOLE_FLAG, VEND, VMEAN, VPEAK and MIC to host for further processing.

Those skilled in the art will appreciate that the invention may be accomplished with circuits other than those particularly depicted and described in connection with FIGS. 6–8. These figures represent just one of many possible implementations of a Doppler ultrasound system in accordance with the invention. Likewise, the invention may be accomplished using process steps other than those particularly depicted and described in connection with FIG. 9–12.

Those skilled in the art will also understand that each of the circuits whose functions and interconnections are described in connection with FIGS. 6–8 is of a type known in the art. Therefore, one skilled in the art will be readily able to adapt such circuits in the described combination to practice the invention. Particular details of these circuits are not critical to the invention, and a detailed description of the internal circuit operation need not be provided. Similarly, each one of the process steps described in connection with FIGS. 9–12 will be understood by those skilled in the art, and may itself be a sequence of operations that need not be described in detail in order for one skilled in the art to practice the invention.

It will be appreciated that, although specific embodiments of the invention have been described for purposes of illustration, various modifications may be made without deviating from the spirit and scope of the invention. For example, a user interface in accordance with the present invention may be provided by means other than a video display, such as a printer or other visual display device. Those skilled in the art will also appreciate that many of the advantages associated with these circuits and processes described above may be provided by other circuit configurations and processes. Accordingly, the invention is not limited by the particular disclosure above, but instead the scope of the invention is determined by the following claims.

The invention is claimed is:

1. A Doppler ultrasound system, comprising:
   an ultrasound probe to emit ultrasound signals along an ultrasound beam axis and detect reflected signals; and
   a processor coupled to the ultrasound probe and operable to generate Doppler ultrasound data from the detected reflected signals and process the Doppler ultrasound data to calculate blood flow data, including blood flow velocity data and detected Doppler signal power data, for a plurality of locations along the ultrasound beam axis and for a plurality of time intervals, the processor further operable to identify from the blood flow data locations along the ultrasound beam axis at which blood flow having a hemodynamic characteristic is present.

2. The Doppler ultrasound system of claim 1, further comprising a graphical display coupled to the processor to display the blood flow velocity data and the detected Doppler signal power data as blood flow information indicative of the locations along the ultrasound beam axis at which blood flow is detected and the locations at which blood flow having the hemodynamic characteristic is present.

3. The Doppler ultrasound system of claim 2, further comprising a display driver coupled to the processor and the graphical display, the display driver controlling the graphical display to display the blood flow information for the plurality of locations as having a first or second color based on the blood flow velocity data and having a color characteristic that varies based on the detected Doppler signal power data, the display driver further controlling the graphical display to display the locations at which blood flow having the hemodynamic characteristic as regions of a third color.

4. The Doppler ultrasound system of claim 3 wherein the color characteristic that varies based on the detected Doppler signal power data comprises color brightness.

5. The Doppler ultrasound system of claim 1 wherein the processor is operable to identify locations along the ultrasound beam axis at which blood flow having the hemodynamic characteristic is present by determining from the blood flow velocity data blood flow having a mean blood flow velocity in excess of a velocity threshold value.

6. The Doppler ultrasound system of claim 1 wherein the processor is operable to identify locations along the ultrasound beam axis at which blood flow having the hemodynamic characteristic is present by calculating a value for a hemodynamic parameter from the blood flow velocity data for a set of time intervals and comparing the value to a threshold value.

7. A Doppler ultrasound system, comprising:
   an ultrasound probe to emit ultrasound signals and detect reflected signals therefrom; and
   a processor coupled to the ultrasound probe and operable to process the detected reflected signals and calculate therefrom blood flow data for a plurality of locations at a plurality of time intervals, the processor further operable to identify locations at which blood flow having a hemodynamic characteristic is present based on the calculated blood flow data.

8. The Doppler ultrasound system of claim 7, further comprising a graphical display coupled to the processor to display the blood flow data as blood flow information indicative of the locations at which blood flow is detected and the locations at which blood flow having the hemodynamic characteristic is present.

9. The Doppler ultrasound system of claim 8 wherein the processor is operable to calculate from detected reflected signals blood flow velocity data and detected Doppler signal power data for the plurality of locations at the time intervals.

10. The Doppler ultrasound system of claim 9, further comprising a display driver coupled to the processor and the graphical display, the display driver controlling the graphical display to display the blood flow data for the plurality of locations as having a first or second color based on the blood flow velocity data and having a color characteristic that varies based on the detected Doppler signal power data, the display driver further controlling the graphical display to display the locations at which blood flow having the hemodynamic characteristic as regions of a third color.

11. The Doppler ultrasound system of claim 10 wherein the color characteristic comprises color brightness.

12. The Doppler ultrasound system of claim 9 wherein the processor is operable to calculate the blood flow velocity data from the blood flow data for a set of time intervals, and to identify locations at which blood flow having the hemodynamic characteristic is present by calculating a value representative of a hemodynamic parameter from a plurality of the blood flow velocity data.

13. The Doppler ultrasound system of claim 7 wherein the processor is operable to identify locations at which blood flow having the hemodynamic characteristic by calculating from the blood flow data a value representing a hemodynamic parameter and comparing the value to a threshold value.

14. A Doppler ultrasound system, comprising:
   an ultrasound probe to emit ultrasound signals and detect reflected signals therefrom;
   an ultrasound processor coupled to the ultrasound probe and operable to process the detected reflected signals and generate therefrom blood flow data for a plurality of locations as a function of time, the processor further operable to identify locations at which blood flow satisfying a hemodynamic criterion is present based on the blood flow data; and
   a user interface coupled to the processor to provide blood flow information based on the blood flow data, the blood flow information representative of detected blood flow and the presence of the hemodynamic characteristic.

15. The Doppler ultrasound system of claim 14 wherein the user interface comprises a graphical display coupled to the processor to display the blood flow velocity data and the detected Doppler signal power data as blood flow information indicative of the locations at which blood flow is detected and the locations at which blood flow satisfying the hemodynamic criterion is present.

16. The Doppler ultrasound system of claim 15 wherein the ultrasound processor is operable to calculate from the detected reflected signals blood flow velocity data representative of blood flow velocity for the plurality of locations at the time intervals.

17. The Doppler ultrasound system of claim 16, further comprising a display driver coupled to the ultrasound processor and the graphical display, the display driver controlling the graphical display to display the blood flow information for the plurality of locations as having a first or second color based on the blood flow velocity data and a color intensity based on the blood flow velocity relative to a mean blood flow velocity, and the locations at which blood flow satisfying the hemodynamic criterion as regions of a third color.

18. The Doppler ultrasound system of claim 17 wherein the color characteristic comprises color brightness.

19. The Doppler ultrasound system of claim 16 wherein the ultrasound processor is operable to calculate from the detected reflected signals detected Doppler signal power data for the plurality of locations as a function of time.

20. The Doppler ultrasound system of claim 16, further comprising a display driver coupled to the ultrasound processor and the graphical display, the display driver controlling the graphical display to display the blood flow information for the plurality of locations as having a first or second color based on the blood flow velocity data and having a color characteristic that varies based on the detected Doppler signal power data, the display driver further controlling the graphical display to display the locations at which blood flow satisfying the hemodynamic criterion as regions of a third color.

21. The Doppler ultrasound system of claim 14 wherein the processor is operable to identify locations at which blood flow satisfying a hemodynamic criterion is present by calculating a value from the blood flow data for a plurality of time intervals and comparing the value to a threshold value.

22. In a Doppler ultrasound system having a ultrasound transducer emitting ultrasound signals, a method for processing detected reflected signals comprising:

processing the detected reflected signals and calculating therefrom blood flow data for a plurality of locations along an ultrasound beam axis and for a plurality of time intervals;

identifying locations along the ultrasound beam axis at which blood flow having a hemodynamic characteristic is present from the calculated blood flow data; and generating from the blood flow data blood flow information representative of detected blood flow and the presence of the hemodynamic characteristic.

23. The method of claim 22 wherein generating the blood flow information comprises generating display data indicative of the locations at which blood flow is detected and the locations at which blood flow having the hemodynamic characteristic is present.

24. The method of claim 23 wherein calculating from the detected reflected signals blood flow data comprises calculating blood flow velocity data representative of blood flow velocity for the plurality of locations at the time intervals.

25. The method of claim 24, further comprising displaying the blood flow data as having a first or second color based on the blood flow velocity data and having a color characteristic that varies based on the blood flow velocity relative to a mean blood flow velocity, and the locations at which blood flow satisfying the hemodynamic criterion as regions of a third color.

26. The method of claim 25 wherein the color characteristic comprises color brightness.

27. The method of claim 24 wherein calculating from the detected reflected signals blood flow data further comprises calculating detected Doppler signal power data for the plurality of locations at the plurality of time intervals.

28. The method of claim 27, further comprising displaying the blood flow data as having a first or second color based on the blood flow velocity data and a color intensity based on the detected Doppler signal power data, and the locations along the ultrasound beam axis at which blood flow satisfying the hemodynamic criterion as regions of a third color.

* * * * *